US010028829B2

(12) United States Patent
Li

(10) Patent No.: US 10,028,829 B2
(45) Date of Patent: *Jul. 24, 2018

(54) VALVE HOLDER WITH LEAFLET PROTECTION

(71) Applicant: St. Jude Medical, Cardiology Division, Inc., St. Paul, MN (US)

(72) Inventor: Xue Mei Li, Shoreview, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 42 days.

This patent is subject to a terminal disclaimer.

(21) Appl. No.: 15/279,692

(22) Filed: Sep. 29, 2016

(65) Prior Publication Data

US 2017/0014231 A1    Jan. 19, 2017

Related U.S. Application Data

(63) Continuation of application No. 14/198,846, filed on Mar. 6, 2014, now Pat. No. 9,480,563.

(60) Provisional application No. 61/775,007, filed on Mar. 8, 2013.

(51) Int. Cl.
*A61F 2/24* (2006.01)

(52) U.S. Cl.
CPC .......... *A61F 2/2427* (2013.01); *A61F 2/2412* (2013.01)

(58) Field of Classification Search
CPC .......... A61F 2/24; A61F 2/2427; A61F 2/243; A61F 2/2436; A61F 2/2439; A61F 2/2409
See application file for complete search history.

(56) References Cited

U.S. PATENT DOCUMENTS

| 3,409,013 | A | 11/1968 | Berry |
| 4,182,446 | A | 1/1980 | Penny |
| 4,275,469 | A | 6/1981 | Gabbay |
| 4,491,986 | A | 1/1985 | Gabbay |
| 4,759,758 | A | 7/1988 | Gabbay |
| 4,865,600 | A | 9/1989 | Carpentier et al. |
| 4,878,906 | A | 11/1989 | Lindemann et al. |
| 4,922,905 | A | 5/1990 | Strecker |
| 4,994,077 | A | 2/1991 | Dobben |
| 5,236,450 | A | 8/1993 | Scott |
| 5,411,552 | A | 5/1995 | Andersen et al. |
| 5,443,502 | A | 8/1995 | Caudillo et al. |

(Continued)

FOREIGN PATENT DOCUMENTS

| DE | 19857887 A1 | 7/2000 |
| DE | 10121210 A1 | 11/2002 |

(Continued)

OTHER PUBLICATIONS

Catheter-implanted prosthetic heart valves, Knudsen, L.L., et al., The International Journal of Artificial Organs, vol. 16, No. 5 1993, pp. 253-262.

(Continued)

*Primary Examiner* — Katrina Stransky
(74) *Attorney, Agent, or Firm* — Lerner, David Littenberg, Krumholz & Mentlik, LLP

(57) ABSTRACT

An implantation device for a prosthetic heart valve includes a valve holder for maintaining the prosthetic heart valve in a closed configuration and at least one protective sheet coupled to the valve holder, the at least one protective sheet being configured to cover a leaflet of the heart valve during implantation.

19 Claims, 8 Drawing Sheets

(56) References Cited

U.S. PATENT DOCUMENTS

| | | |
|---|---|---|
| 5,476,510 A | 12/1995 | Eberhardt et al. |
| 5,480,423 A | 1/1996 | Ravenscroft et al. |
| 5,776,187 A | 7/1998 | Krueger et al. |
| 5,800,531 A | 9/1998 | Cosgrove et al. |
| 5,824,068 A | 10/1998 | Bugge |
| 5,855,601 A | 1/1999 | Bessler et al. |
| 5,906,642 A | 5/1999 | Caudillo et al. |
| 5,935,163 A | 8/1999 | Gabbay |
| 5,961,549 A | 10/1999 | Nguyen et al. |
| 6,019,790 A | 2/2000 | Holmberg et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,409,758 B2 | 6/2002 | Stobie et al. |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,685,625 B2 | 2/2004 | Gabbay |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,869,444 B2 | 3/2005 | Gabbay |
| 6,893,460 B2 | 5/2005 | Spenser et al. |
| 6,908,481 B2 | 6/2005 | Cribier |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,374,573 B2 | 5/2008 | Gabbay |
| 7,381,218 B2 | 6/2008 | Schreck |
| 7,452,371 B2 | 11/2008 | Pavcnik et al. |
| 7,524,331 B2 | 4/2009 | Birdsall |
| RE40,816 E | 6/2009 | Taylor et al. |
| 7,585,321 B2 | 9/2009 | Cribier |
| 7,731,742 B2 | 6/2010 | Schlick et al. |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| D684,692 S | 6/2013 | Braido |
| 9,480,563 B2 * | 11/2016 | Li .................. A61F 2/2412 |
| 2002/0013621 A1 | 1/2002 | Stobie et al. |
| 2002/0036220 A1 | 3/2002 | Gabbay |
| 2002/0133226 A1 | 9/2002 | Marquez et al. |
| 2003/0023303 A1 | 1/2003 | Palmaz et al. |
| 2003/0125805 A1 | 7/2003 | Johnson et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0148017 A1 | 7/2004 | Stobie |
| 2005/0096726 A1 | 5/2005 | Sequin et al. |
| 2005/0256566 A1 | 11/2005 | Gabbay |
| 2006/0008497 A1 | 1/2006 | Gabbay |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244551 A1 | 10/2007 | Stobie |
| 2007/0260305 A1 | 11/2007 | Drews et al. |
| 2007/0288087 A1 | 12/2007 | Fearnot et al. |
| 2008/0021552 A1 | 1/2008 | Gabbay |
| 2008/0033545 A1 | 2/2008 | Bergin |
| 2008/0039934 A1 | 2/2008 | Styrc |
| 2008/0071367 A1 | 3/2008 | Bergin et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0076599 A1 | 3/2009 | Bergin |
| 2009/0112309 A1 | 4/2009 | Jaramillo et al. |
| 2009/0138079 A1 | 5/2009 | Tuval et al. |
| 2009/0259305 A1 | 10/2009 | Lane et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2011/0029072 A1 | 2/2011 | Gabbay |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2850008 A1 | 7/2004 |
| FR | 2847800 B1 | 10/2005 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 10008548 A2 | 1/2010 |

(56) References Cited

FOREIGN PATENT DOCUMENTS

| WO | 10008549 A1 | 1/2010 |
|----|-------------|--------|
| WO | 10096176 A1 | 8/2010 |
| WO | 10098857 A1 | 9/2010 |

OTHER PUBLICATIONS

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243, filed Sep. 20, 2010.

\* cited by examiner

VALVE HOLDER WITH LEAFLET PROTECTION

CROSS-REFERENCES TO RELATED APPLICATIONS

The present application is a continuation of U.S. patent application Ser. No. 14/198,846, filed Mar. 6, 2014, which claims the benefit of the filing date of U.S. Provisional Application No. 61/775,007, filed on Mar. 8, 2013, the disclosure of which is hereby incorporated herein by reference.

BACKGROUND OF THE INVENTION

This invention relates to prosthetic heart valves, and more particularly to holders and other protection devices for prosthetic heart valve leaflets that may be useful during implantation in a patient.

There is increasing interest in artificial, prosthetic heart valves that use tissue material for the leaflets of the valve. Such valves tend to be less thrombogenic than mechanical prosthetic heart valves. This can reduce or eliminate the need for a patient who has received such prosthesis to take anti-coagulant medication on a long-term basis. Tissue-based heart valves may also have other advantages, such as quieter operation than mechanical valves. Because of the interest in such valves, improvements to them are greatly desired. Improved methods of making such valves are also sought. Efforts have also being made to find a more durable flexible leaflet material than tissue, such as polymer valves.

Despite the various improvements that have been made to prosthetic heart valves, conventional devices, systems, and methods suffer from some shortcomings. For example, in conventional heart valve replacement surgery, the leaflets of a replacement valve may be damaged during implantation. While a mechanical valve may be robust and not sensitive to scratches and/or scrapes from surgical instruments during implantation, the leaflets of polymer valves may be sensitive to such scratches. Valve durability and/or function may be compromised if sharp scratches are in stress sensitive locations, and may lead to tearing of the leaflet and limiting or impeding proper valve function.

There therefore is a need for further improvements to the devices, systems, and methods for prosthetic heart valve delivery and implantation. Among other advantages, the present invention may address one or more of these needs.

SUMMARY OF THE INVENTION

In some embodiments, an implantation device for a prosthetic heart valve includes a valve holder for maintaining the prosthetic heart valve in a closed configuration and at least one protective sheet coupled to the valve holder, the at least one protective sheet being configured to cover a leaflet of the heart valve during implantation.

In some examples, the at least one protective sheet includes three protective sheets. The at least one protective sheet may include a protective sheet for each leaflet of the prosthetic heart valve. The at least one protective sheet may be comprised of at least one of Ultem, Delrin, Udel, PEEK, etc. The valve holder may include suture features for coupling the at least one protective sheet to the heart valve. Each protective sheet may include a leg coupleable to a ring of a heart valve at a suture feature. The valve holder may include a slot for receiving a handle.

In some embodiments, an implantation device for a prosthetic heart valve includes a valve holder for maintaining the prosthetic heart valve in a closed configuration, a chimney coupled to the valve holder, the chimney defining a lumen and at least one protective sheet coupled to the valve holder, and extending through the lumen of the chimney.

In some examples, the prosthetic heart valve is a mitral valve. The at least one protective sheet may include three protective sheets. The at least one protective sheet may include a protective sheet for each leaflet of the prosthetic heart valve. The at least one protective sheet may be comprised of at least one of Ultra-high-molecular-weight polyethylene (UHMWPE), PTFE, polyurethane, etc. The valve holder may include suture features for coupling the at least one protective sheet to the heart valve. Each protective sheet may include a leg coupleable to a ring of a heart valve at a suture feature on the leg. The valve holder may include a slot for receiving a handle. The at least one protective sheet may be configured to wrap around the prosthetic heart valve. The valve holder may include suture features for coupling the at least one protective sheet to the valve holder. The implantation device may further include a sheet clamp coupled to the valve holder for clamping a portion of the at least one sheet protector. The sheet clamp may include complementary upper and lower portions configured to retain a protective sheet between the upper and lower portions. The upper and lower portions may include complementary suture holes for coupling the upper portion to the lower portion via sutures.

BRIEF DESCRIPTION OF THE DRAWINGS

Various embodiments of the present invention are disclosed herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION

Figure 1:
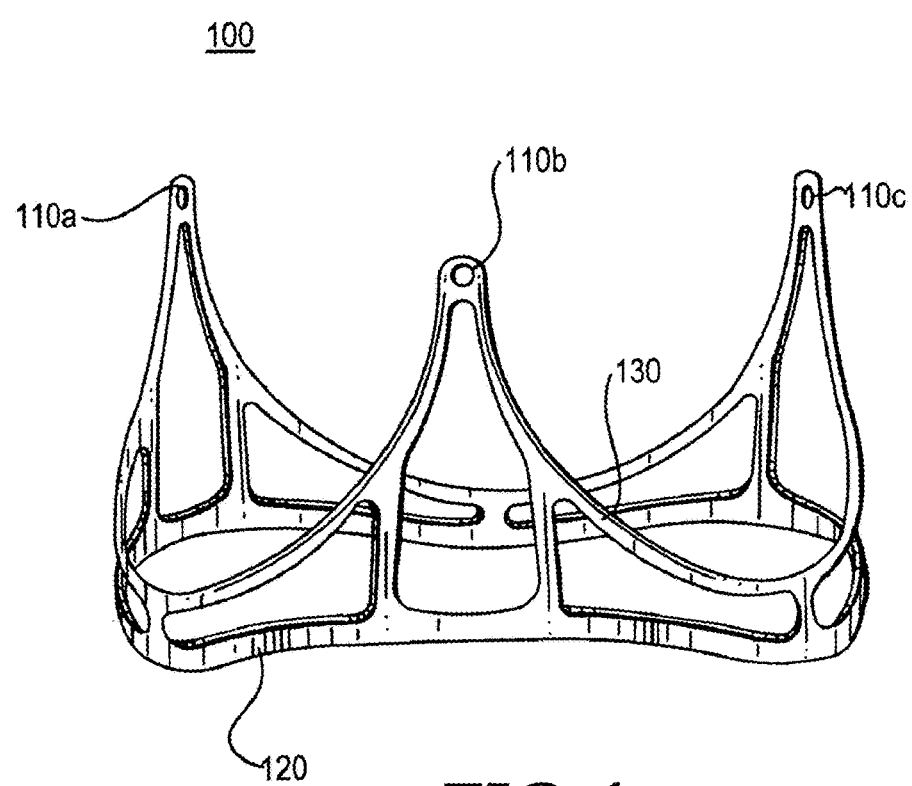
FIG. 1 is a perspective view of an example of a stent frame of a prosthetic heart valve.

An illustrative embodiment of a first component 100 of an artificial heart valve in accordance with the invention is shown in FIG. 1. Component 100 is a hollow, annular, stent-like structure on frame. Frame 100 is typically made of metal such as a titanium alloy (e.g., Ti 6Al-4V ELI Grade 5) or a polymeric materials such as PEEK. A typical technique for making frame 100 is to cut it from a tube using a laser. Frame 100 is then typically electro-polished. In case of polymeric materials, frame 100 may be injection molded or machined.

Because the valve of the illustrative embodiment described herein is a tricuspid valve (e.g., a valve that includes three leaflets for use in replacing a patient's aortic valve), frame 100 has three commissure portions or regions 110a, 110b, and 110c that are equally spaced from one another around the circumference of the frame. Each commissure portion stands up from the annularly continuous base portion of the frame. The base portion includes a lower-most, blood-inflow edge portion 120. This blood-inflow edge portion may be scalloped as one proceeds around the frame to approximately match the natural scallop of the native aortic valve annulus. In particular, this scallop rises in the vicinity of each commissure region, and it falls between each annularly adjacent pair of commissures.

Frame 100 also includes an annularly continuous blood-outflow edge portion 130 (which merges with and becomes part of each commissure region 110 at the commissures). Outflow edge portion 130 is much more deeply scalloped than the inflow edge portion. In particular, outflow edge portion 130 rises adjacent each commissure 110 (actually merging into each commissure as noted above), and falls between each annularly adjacent pair of commissures.

The inflow edge 120, outflow edge 130, and flexibility of frame 100 are designed to help ensure proper opening and coaptation of the finished valve in use. (Coaptation is the coming together of the outflow portions of the valve leaflets when the valve is closed.) Frame 100 is further designed to decrease maximum stresses in the frame in use, which gives the finished valve an increased safety factor.

Although titanium is mentioned above as a typical material from which frame 100 can be made, other materials are also possible. Some examples of other materials that may be suitable for use in making frame 100 include Elgiloy® MP35N or polymers such as PEEK or acetal.

Figure 2:
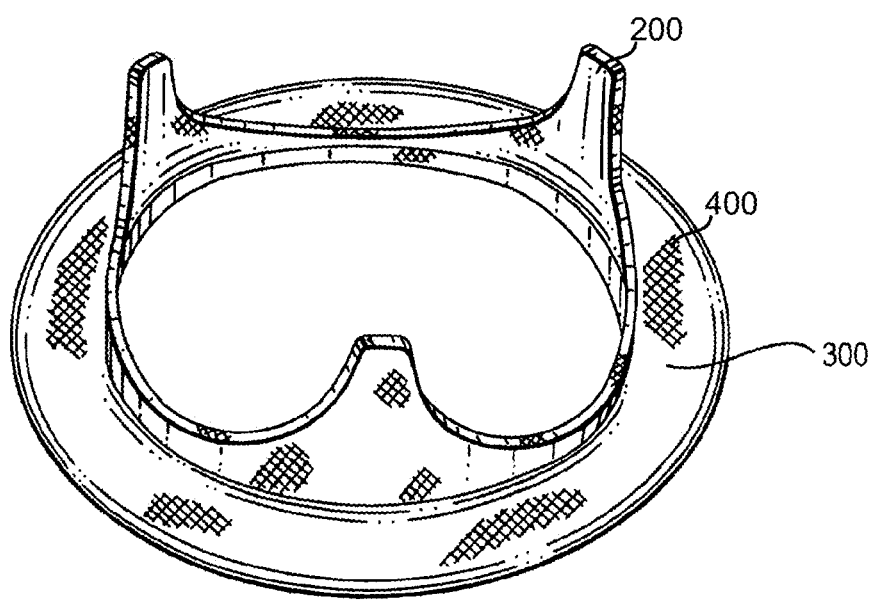
FIG. 2 is a perspective view of an assembly of the stent frame of FIG. 1 with a silicone ring and fabric covering.

FIG. 2 shows an assembly 500 that includes frame 100 with several coverings. A first, sleeve-like fabric covering 200 may be disposed over the top of each commissure post as seen in FIG. 2. Fabric commissure tip covers 200 help reduce the possibility that the commissure tips of the frame may poke through subsequently added components. An illustrative fabric that is suitable for use in making coverings 200 is REEMAY® fabric, which is a spun form of polyester. Each tip cover 200 may be secured to the associated commissure tip with sutures.

Frame 100 (with coverings 200) may also include a ring 400 placed coaxially around the outside of a lower portion of a fabric tube 300. Ring 400 may be located outside the inflow edge portion 120 of frame 100. The upper portion of sleeve 300 may then be pulled down over the outside of components 100 and 400 and pulled tightly enough to conform to outflow edge portion 130 as shown in FIG. 2.

Figure 5:
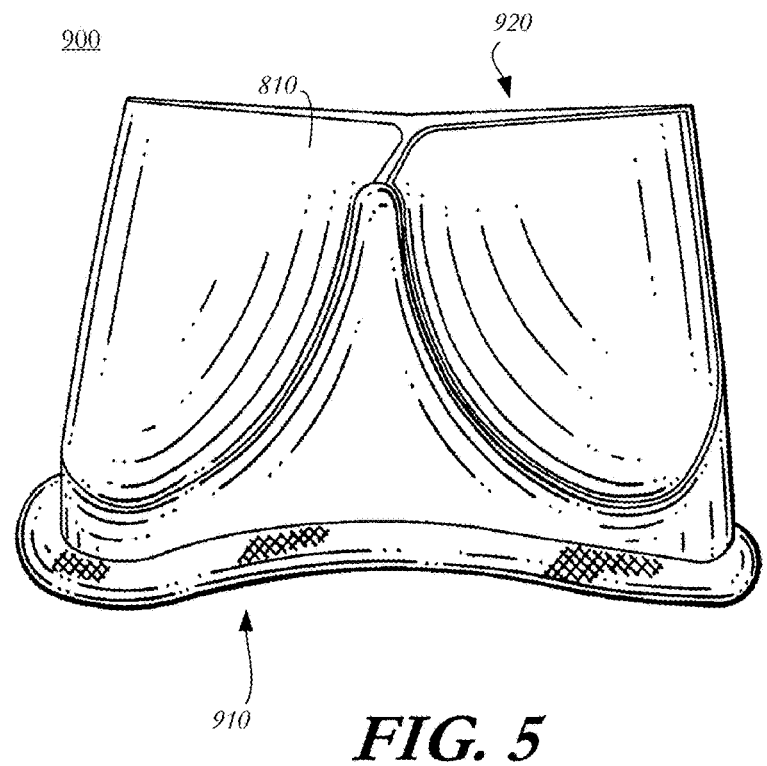
FIG. 5 is a perspective of an illustrative embodiment of a completed prosthetic heart valve.

Sutures may be used to hold the above-described components together in the condition shown in FIG. 5. In particular, all of components 100, 200, and 400 are completely covered inside and out by fabric 300. Ring 400 is located adjacent inflow edge portion 120 and follows the scalloping of inflow edge portion 120 all the way around assembly 500. The upper portion of fabric 300 conforms closely to frame 100 above ring 400, and in particular, the upper portion of the fabric follows the scalloped outflow edge portion 130 all the way around assembly 500.

Figure 3A:
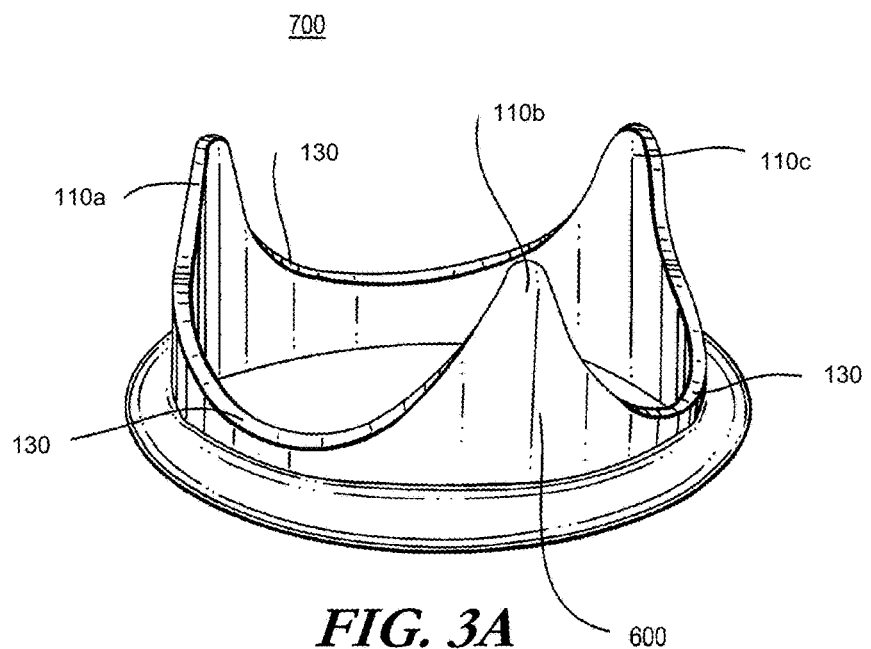
FIGS. 3A and 3B are respectively perspective top and bottom views of the prosthetic heart valve of FIG. 2.
Figure 3B:
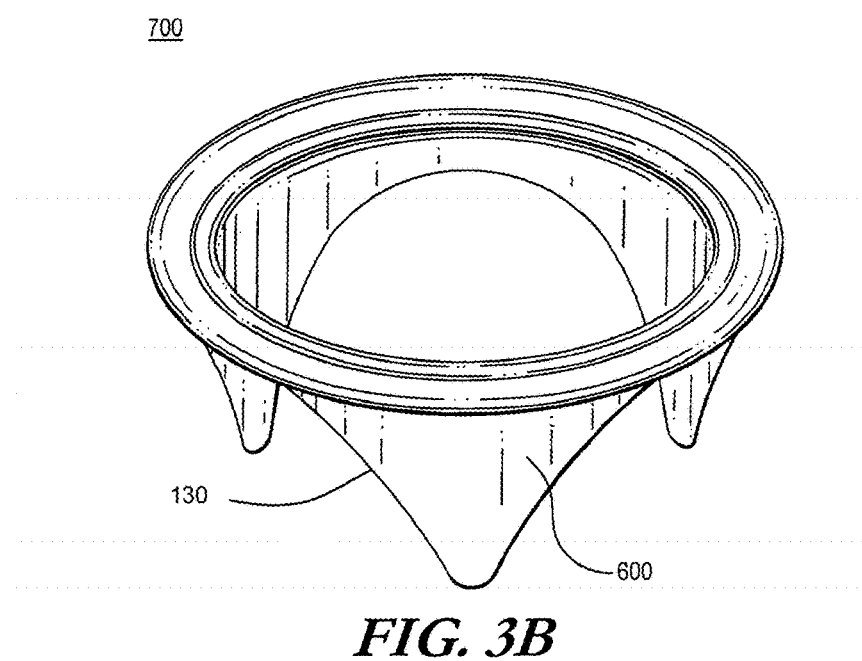

FIGS. 3A and 3B illustrate still further possible components and steps in the manufacture of the illustrative embodiment being described. In particular, these figures illustrate the addition of porcine pericardium tissue 600 over assembly 500, both inside and out, to produce assembly 700. One of the purposes of this is to enhance durability of the finished valve. Another purpose is to reduce thrombogenicity of the finished valve. Sutures may be used to secure tissue 600 to assembly 500 as shown in FIGS. 3A and 3B. Apart from somewhat thickening assembly 700 as compared to assembly 500, the addition of tissue 600 does not significantly change the shape of any portion of the structure.

Although porcine pericardium is mentioned above for component 600, other types of tissue may be used instead if desired. Examples of such other possible tissue for component 600 include any mammalian pericardium (e.g., equine or bovine pericardium).

Figure 4:
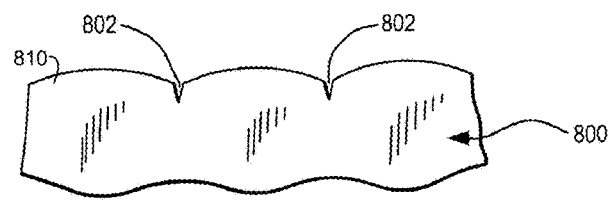
FIG. 4 is a perspective view of a tissue sheet prior to assembly with the other components.

FIG. 4 illustrates a further possible component and steps in the manufacture of the illustrative embodiment being described. As shown in FIG. 4, component 800 is a sheet of bovine pericardium that has been die cut to a shape that can be used to form all three leaflets of a finished valve. Note that the lower edge of sheet 800 (as viewed in FIG. 4) is scalloped to conform to the blood-inflow edge (like 120 in FIG. 1) of the finished valve. The upper portion of sheet 800 (as viewed in FIG. 4) will form the three leaflets 810 of the valve. There are shallow downward cuts 802 between the individual leaflet portions adjacent the upper edge of sheet 800, but sheet 800 remains intact so that this single sheet of tissue can be used to form all three leaflets 810 in the finished valve.

Although bovine pericardium is mentioned above for sheet 800, other types of tissue may be used instead as desired. Examples of such other possible tissue for sheet 800 include any mammalian pericardium (e.g., equine or porcine pericardium).

Although tissue is mentioned above for sheet 800, polymeric materials may be used instead as desired. Examples of such polymeric materials for sheet 800 include polyurethane, silicone rubber, Poly(styrene-b-isobutylene-b-styrene), or other suitable materials.

FIG. 5 illustrates a complete prosthetic heart valve 900 after assembly of leaflets 810 to the frame 100. The complete prosthetic heart valve includes an inflow end 910 and an outflow end 920. In use, valve 900 has the operating characteristics described in the preceding paragraphs. Ideally, the coaptation section of each leaflet may range in size as a particular valve design demands, but generally, will be sufficient to provide some tolerance, or ability to form a coaptation junction even if the shape of the valve is distorted during placement.

Figure 6:
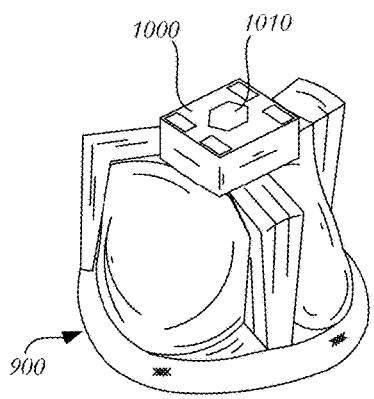
FIG. 6 is a perspective view of a prosthetic heart valve attached to a holder.

A valve holder may be useful in implanting the replacement valve. FIG. 6 illustrates a valve holder 1000 attached to valve 900. As seen in FIG. 6, valve holder 1000 maintains valve 900 in a closed condition during implantation and includes a slot 1010 for coupling holder 1000 to a handle 1020 FIG. 7.

Figure 7:
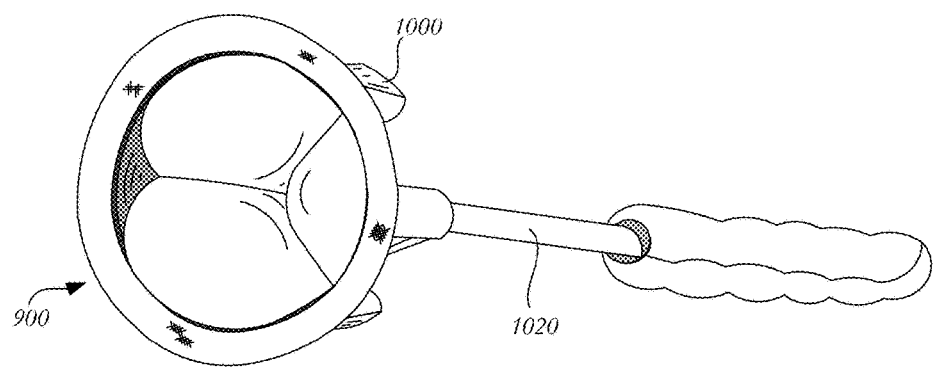
FIG. 7 is a perspective view of a handle attached to a prosthetic heart valve for implanting the valve.

As will be appreciated from FIG. 7, during surgery, a surgeon may manipulate handle 1020, which is attached to holder 1000, to position valve 900 into different locations and orientations to facilitate the operation. After the valve 900 has been positioned, the holder 1000 may be detached from the valve 900 before the chest is closed.

As previously described, during implantation, scratches and/or scrapes from surgical instruments may damage the valve portion. This may compromise valve durability and/or function if sharp scratches develop in the stress sensitive locations, and especially if the leaflets of the valve are made of polymeric materials. To protect the leaflets from these scratches, a valve implantation device having leaflet protective elements may be used to cover the vulnerable leaflets.

Figure 8:
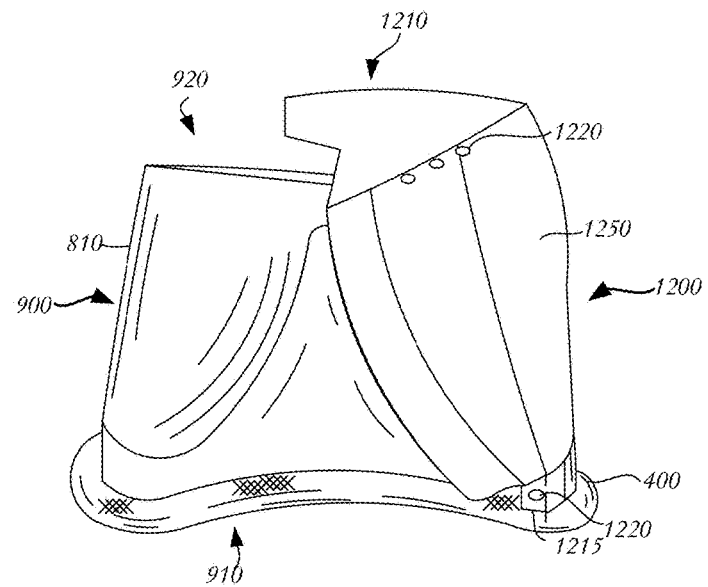
FIG. 8 is a highly schematic perspective view of a portion of an aortic implantation device having a protective sheet disposed over one leaflet of a heart valve.

FIG. 8 illustrates a portion of an aortic valve implantation device 1200 having a protective sheet 1250 disposed over one leaflet 810 of valve 900. Protective sheet 1250 may be formed integrally with aortic valve holder 1210. Protective sheet 1250 may be formed of any suitable material including Ultem®, Delrin®, Udel®, PEEK, or suitable combinations thereof.

For aortic valves, a protective sheet 1250 may be attached to ring portion 400, as seen in FIG. 8, and coupled to other protective sheets 1250 near the outflow edge of valve 900 to form the structure platform of the holder. Each protective sheet 1250 may terminate in a leg 1215 near the inflow end 910 of valve 900. Implantation device 1200 may include a protective sheet 1250 for each leaflet 810. Thus, implantation device 1200 may include two, three or more protective sheets 1250. The protective sheets 1250 may be unitarily formed as a single piece. Alternatively, protective sheets 1250 may be formed as three separate sheets and their edges joined at the top of implantation device 1200 near outflow end 920.

As seen in FIG. 8, each protective sheet 1250 may further include suture features 1220 near both the inflow end 910 and outflow end 920 for attaching the protective sheet 1250 to the valve 900. Suture features 1220 may be formed as eyelets and may be disposed near the inflow end 910 so that protective sheet 1250 may be attached to ring 400. At outflow end 920, suture features 1220 may be disposed at locations between the commissure portions.

Figure 9:
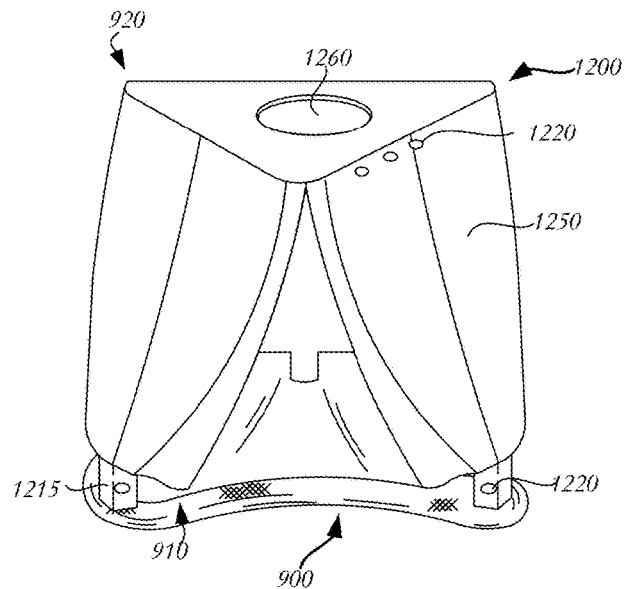
FIG. 9 is a highly schematic perspective view of an implantation device having three protective sheets, each protective sheet being coupled to the ring portion of a heart valve.

FIG. 9 illustrates an implantation device 1200 having three protective sheets 1250, each protective sheet 1250 being coupled to the ring portion 400 and attached to one of the other two protective sheets 1250 at edges near the outflow end 920. Protective sheets 1250 may include suture features 1220 for attaching to valve 900 near the outflow and inflow ends. A slot 1260 or other suitable connection mechanism may be provided for coupling a handle 1020 to the implantation device 1200 to implant the heart valve.

In use, an implantation device 1200 may be coupled to prosthetic heart valve 900 via sutures at suture features 1220 or through any other suitable method. Handle 1020 may be attached to implantation device 1200 at slot 1260 and a surgeon or user may maneuver handle 1020 as necessary to implant the heart valve within the patient. Once the heart valve 900 has reached the desired destination with leaflets 810 protected from the environment by the protective sheets 1250, a surgeon or user may cut loose sutures at suture features 1220 to decouple the implantation device 1200 from valve 900 and remove the implantation device from the patient's body, leaving valve 900 at the desired site. It will be understood that implantation device 1200 may be useful for protecting both polymer and tissue heart valves.

The examples illustrated above outline valve holders used for aortic heart valve replacement. Leaflet protection may also be desired for mitral heart valves. It will be understood that because of the different positioning and orientation of the aortic and mitral heart valves, a different configuration of the valve holder is desirable for mitral valves. Specifically, in the aortic valve blood flows upward from the left ventricle to the aorta. In surgery, the aorta may be cut open, so that the surgeon faces the outflow of the valve. Conversely, in the mitral valve, blood flows downward from the left atrium to the left ventricle. In surgery, the atrium may be cut open, so that the surgeon faces the inflow of the valve. This results in inverse positions of the valve and holder.

Figure 10:
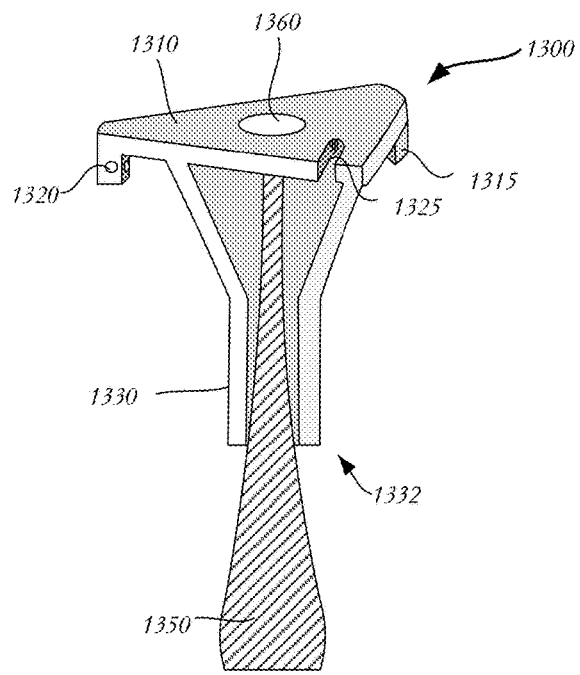
FIG. 10 is a perspective view in partial cross-section of an implantation device for coupling to a mitral valve.

In order to accommodate this difference, a second embodiment of the implantation device will be described which allows for the holding and implantation of a mitral valve. FIG. 10 illustrates an implantation device 1300 for coupling to a mitral valve (not shown). As seen in FIG. 10, implantation device 1300 generally includes mitral valve holder 1310, chimney 1330 and protective sheets 1350.

Mitral valve holder 1310 maintains the prosthetic valve in a closed condition during implantation and includes a slot 1360 for coupling implantation device 1300 to a handle (not shown). As seen in FIG. 10, mitral valve holder 1310 may be configured in the shape of a triangle having three legs 1315. Alternatively, mitral valve holder 1310 may be circular. Each leg 1315 may include one or more suture features 1320. Additionally, mitral valve holder 1310 may include one or more slots 1325 for accepting protective sheets 1350.

A chimney 1330 may be coupled to mitral valve holder 1310. Chimney 1330 may be formed as a hollowed structure for housing a portion of protective sheets 1350, which may be coupled to the base of holder 1310 at one end via a sheet clamp (not shown). The sheet clamp will be described in more detail below with reference to FIGS. 12A and 12B.

Chimney 1330 may be sized to accept a mitral valve. Ends of a plurality of protective sheets 1350 may extend from the proximal end 1332 of chimney 1330. In at least some examples, three protective sheets 1350 may extend from chimney 1330, one for each leaflet to be protected. It will be understood that any number of protective sheets 1350 may be utilized, including one, two, three, four, five, six or more protective sheets 1350, with more than one protective sheet being disposed over any given leaflet.

Figure 11:
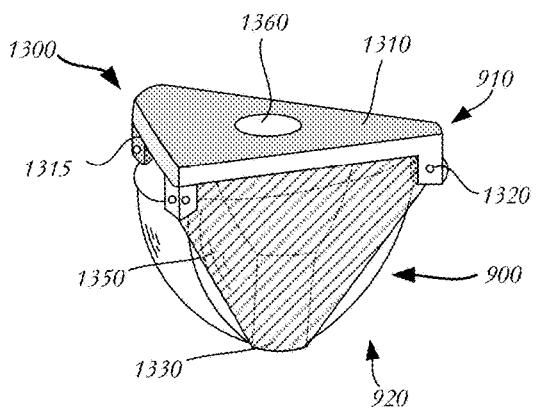
FIG. 11 is a highly schematic perspective view of a prosthetic mitral heart valve loaded within the implantation device of FIG. 10.

FIG. 11 illustrates a prosthetic mitral heart valve 900 loaded within implantation device 1300. As seen in FIG. 11, mitral valve holder 1310 may include slot 1360 for coupling to a handle (not seen) so that the holder may be used to implant a mitral valve.

Mitral heart valve 900 may be disposed about chimney 1330 with the inflow end 910 disposed near valve holder 1310, and outflow end 920 at the proximal end of chimney 1330. Protective sheets 1350 may be attached to the base of holder 1310, extend through chimney 1330 and out the proximal end of the chimney, wrap over valve 900, and mate at the top portion of mitral valve holder 1310. Implantation device 1300 may include any number of protective sheets 1350 as discussed above, each mating at one edge of valve holder 1310 to protect a leaflet 810. Protective sheets 1350 may be attached to valve holder 1310 at suture features 1320 on legs 1315 of valve holder 1310. In this manner, protective sheets 1350 are capable of forming a tent around valve 900 to protect the leaflets 810 during implantation.

Figure 12A:
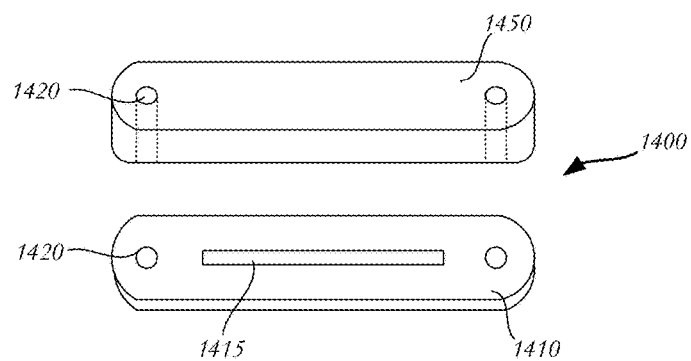
FIG. 12A is an enlarged perspective view of a sheet clamp having a lower portion and an upper portion.

Ends of protective sheet 1350 may be connected to the base of holder 1310 through sheet clamp 1400. FIG. 12A illustrates one example of a sheet clamp 1400 having a lower portion 1410 and an upper portion 1450. Lower portion 1410 may be formed as a body having a sheet slot 1415 for receiving a portion of a protective sheet 1350 and a pair of suture holes 1420. Upper portion 1450 may be formed as a complementary body having a pair of suture holes 1420, but with no slot. Upper portion 1450 may be integrally formed as part of holder 1310, or may be coupled or coupleable to holder 1310 by any method known in the art.

Figure 12B:
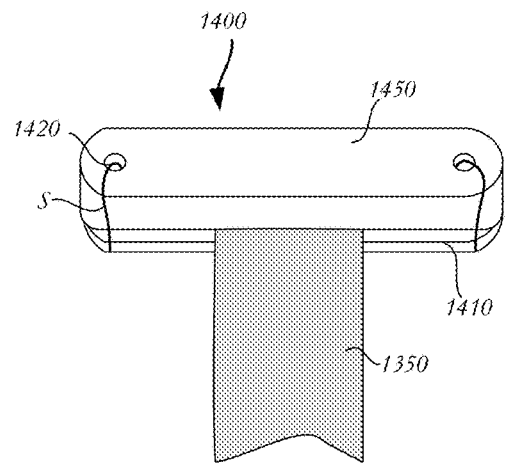
FIG. 12B is an enlarged perspective view of the lower and upper portions of the sheet clamp of FIG. 12A clasped over a protective sheet.

As seen in FIG. 12B, protective sheet 1350 may be passed through sheet slot 1415 of lower portion 1410 and disposed between the lower portion and upper portion 1450. Suture S may be used to tie the two portions together at suture holes 1420, effectively clamping protective sheet 1350 between the two portions. In this manner, one end of protective sheet 1350 may be tied to holder 1310. As described above, the second end of protective sheet 1350 may be wrapped around valve 900 and tied to suture features on holder 1310. Alternatively, both ends of protective sheet 1350 may be held by clamp 1400.

In use, an implantation device 1300 may be coupled to a heart valve 900, in this case a mitral valve, by using clamp 1400. As with the aortic valve, a handle may be attached to implantation device 1300 and a surgeon or user may maneuver the handle as necessary to implant the heart valve within the patient. Once the heart valve 900 has reached the desired destination, with leaflets of the valve protected from the environment by the protective sheets 1350, a surgeon or user may cut loose sutures, thereby loosening clamp 1400. Now that the protective sheet is out of the way, implantation device 1300 may then be decoupled from valve 900 by cutting other sutures that couple the valve to the implantation device 1300. The handle and implantation device, including the clamp and sutures may be removed from the patient's body, leaving valve 900 at the desired site.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An implantation device for a prosthetic heart valve having a plurality of leaflets, comprising:
 a valve holder for maintaining the plurality of leaflets of the prosthetic heart valve in a closed configuration when coupled to the prosthetic heart valve; and
 a plurality of protective sheets each of the plurality of protective sheets extending between a first end coupled to the valve holder, and a second end for coupling to a portion of the prosthetic heart valve via an aperture for receiving a suture therethrough, and extending from a first commissure portion to a second commissure portion of the prosthetic heart valve, the plurality of protective sheets collectively covering the leaflets of the prosthetic heart valve during implantation.

2. The implantation device of claim 1, wherein the plurality of protective sheets includes three protective sheets.

3. The implantation device of claim 1, wherein the plurality of protective sheets includes a protective sheet for each leaflet of the prosthetic heart valve.

4. The implantation device of claim 1, wherein the plurality of protective sheets is comprised of at least one of Ultem, Delrin, Udel, and PEEK.

5. The implantation device of claim 1, wherein each of the plurality of protective sheets includes a leg coupleable to a portion of a prosthetic heart valve.

6. The implantation device of claim 1, wherein the valve holder includes a slot for receiving a handle, and the valve holder is configured and arranged to be removed with the handle after implantation of the prosthetic heart valve.

7. The implantation device of claim 1, wherein each of the plurality of protective sheets are sutured to the valve holder.

8. The implantation device of claim 1, wherein each of the plurality of protective sheets are sutured to the prosthetic heart valve.

9. The implantation device of claim 1, wherein at least one of the plurality of protective sheets covers a majority of a surface of one of the plurality of leaflets.

10. The implantation device of claim 1, wherein at least one of the plurality of protective sheets covers an entire surface of one of the plurality of leaflets.

11. A method of implanting a prosthetic heart valve having a plurality of leaflets in a patient's body, the method comprising:
 providing a valve holder for maintaining the plurality of leaflets of the prosthetic heart valve in a closed configuration when coupled to the prosthetic heart valve; and
 covering the plurality of leaflets with a plurality of protective sheets to protect the prosthetic heart valve, each of the plurality of protective sheets extending between a first end coupled to the valve holder, and a second end for coupling to a portion of the prosthetic heart valve via an aperture for receiving a suture therethrough, and extending from a first commissure portion to a second commissure portion of the prosthetic heart valve, the plurality of protective sheets collectively covering the leaflets of the prosthetic heart valve during implantation; and
 introducing the protected prosthetic heart valve to a site of implantation.

12. The method of claim 11, further comprising coupling the plurality of protective sheets to the prosthetic heart valve.

13. The method of claim 12, wherein coupling the plurality of protective sheets to the prosthetic heart valve including suturing each of the plurality of sheets to the prosthetic heart valve.

14. The method of claim 11, wherein covering the plurality of leaflets includes suturing the plurality of protective sheets to the valve holder.

15. The method of claim 11, wherein the valve holder includes a slot, the slot being capable of accepting a handle.

16. The method of claim 15, further comprising coupling the handle to the slot and maneuvering the handle to position the prosthetic heart valve.

17. The method of claim 11, further comprising uncovering the plurality of leaflets by removing the plurality of protective sheets.

18. The method of claim 12, further comprising decoupling the plurality of protective sheets from the valve holder and removing the protective sheets from the patient's body.

19. The method of claim 11, further comprising removing the valve holder from the patient's body.

* * * * *